United States Patent [19]
Fujita et al.

[11] Patent Number: 5,830,666
[45] Date of Patent: Nov. 3, 1998

[54] METHOD OF DETECTING NUCLEIC ACIDS OR THE LIKE

[75] Inventors: Satoshi Fujita, Nisshin; Naoto Kagiyama, Sapporo; Masayoshi Momiyama, Sapporo; Yasumitsu Kondoh, Sapporo; Miho Nishiyauchi, Sapporo, all of Japan

[73] Assignee: Aisin Seiki Kabushiki Kaisha, Kariya, Japan

[21] Appl. No.: 825,462

[22] Filed: Mar. 28, 1997

[30] Foreign Application Priority Data

Mar. 28, 1996 [JP] Japan ................................. 8-074815

[51] Int. Cl.$^6$ ............................ C12Q 1/68; G01N 33/00; C07H 21/00; C07K 1/00
[52] U.S. Cl. ............................. 435/6; 435/21; 435/68.1; 435/968; 436/86; 436/87; 436/89; 436/800; 536/24.3; 530/350
[58] Field of Search ................................ 435/6, 21, 68.1, 435/968; 436/86, 87, 89, 800; 536/24.3; 530/350

[56] References Cited

FOREIGN PATENT DOCUMENTS

| | | |
|---|---|---|
| 0401813 | 12/1990 | European Pat. Off. . |
| 9500660 | 1/1995 | WIPO . |
| 9640983 | 2/1996 | WIPO . |
| 9636729 | 11/1996 | WIPO . |

OTHER PUBLICATIONS

Tang et al., "Synthesis of Fluorescein Magnesium Monophosphate for Determination of Acid Phosphatase," *Huaxue Shiji*(Chinese), 18(3), 179–180 (1996); Chem. Abstr. 126(5), p. 284, Abstr. No. 56775u (Feb. 3, 1997); only Abstract supplied.

Fujita et al., "Efficient Detection of Membrane–Bound Nucleic Acids Using New Fluorescein Derivative," *Chemistry Leters, Issue. No. 12*, 1073–1074 (Dec. 1996).

*Primary Examiner*—Douglas W. Robinson
*Assistant Examiner*—L. Eric Crane
*Attorney, Agent, or Firm*—Burns, Doane, Swecker & Mathis, LLP

[57] ABSTRACT

A method of detecting nucleic acids, proteins, or protein nucleic acid complexes. The method includes binding an enzyme, such as phosphatase, to a specimen of the nucleic acid, protein, or protein nucleic acid complex. The enzyme is then reacted with a fluorescein derivative phosphate ester to obtain a fluorescein derivative phosphate ester hydrolysate. The hydrolysate is then irradiated with excitation light, and the emitted fluorescein is detected.

5 Claims, 1 Drawing Sheet

Fig. 1

METHOD OF DETECTING NUCLEIC ACIDS OR THE LIKE

CROSS-REFERENCE TO RELATED APPLICATIONS

This application claims priority under 35 U.S.C. §119 to Japanese Patent Application No. Hei 08-074815, filed on Mar. 28, 1996, in Japan; the contents of which are hereby incorporated by reference.

BACKGROUND OF THE INVENTION

1. Field of the Invention

The present invention relates to a method of detecting nucleic acids, proteins, protein nucleic acid complexes or the like, using a fluorescent substrate.

2. Description of the Related Art

In many medical or biological fields, the sequencing of nucleic acids is performed using nucleic acid fragment detection methods. In a typical conventional detection method, a nucleic acid probe is labeled with a radioactive isotope and hybridized with a nucleic acid specimen. The nucleic acid is then detected by autoradiography (Sambrook, J., et al., Molecular Cloning, 2d edition, Cold Spring Harbor Laboratory Press).

However, such isotope methods have problems, for example, in that the methods do not provide a sufficiently high three-dimensional resolution power to reveal the positional relationship between adjacent genes (between adjacent sequences of a nucleic acid), and in that the methods require an isotope laboratory with dedicated equipment. These problems have impeded the application and development of this technology.

To overcome such problems, new labeling methods for DNA or RNA have been developed which do not use radioactive isotopes. Examples of the new methods include a calorimetric method described in Proc. Nat'l Acad. Sci., U.S.A., Vol. 80, p. 4045 (Leary, J., et al., 1983); a chemiluminescent method described in Nucleic Acids Res., Vol. 17, p. 5115 (Beck, S., et al., 1989); and a method of detecting nucleic acids or the like described in Japanese Patent Laid-Open No. Hei 4-91799. A DNA detection kit commercially available from Bethesda Research Laboratory also adopts a non-radioactive labeling method.

However, while these methods eliminate some of the problems mentioned above, they fail to surpass the radioisotope method in detection sensitivity. More precisely, the detection sensitivity of the nonradioactive methods is slightly lower; it is $10^{-14}$ g DNA whereas $10^{-15}$ g DNA is achieved by the radioactive detection methods.

SUMMARY OF THE INVENTION

Accordingly, it is an object of the present invention to provide a method of detecting nucleic acids, proteins, protein nucleic acid complexes or the like with an improved sensitivity.

According to one aspect of the present invention, there is provided a method of detecting nucleic acids, proteins, protein nucleic acid complexes or the like. The method comprises the steps of: binding an enzyme to a specimen of nucleic acid, protein, protein nucleic acid complex or the like; reacting a fluorescein derivative monophosphate ester with the enzyme bound to the specimen to form a hydrolysate of the fluorescein derivative monophosphate ester; and irradiating the hydrolysate with excitation light to detect fluorescence emitted from the hydrolysate.

Any fluorescein derivative monophosphate ester known in the art may be used in the method of the present invention. Preferably, the fluorescein derivative monophosphate ester has a structure represented by one of Formulas I to IV below:

(I)

(II)

(III)

(IV)

In this method, the enzyme bound to the specimen is reacted with a fluorescein derivative monophosphate ester, preferably one represented by one of Formulas I to IV. This enzyme-substrate reaction breaks the ester linkage of the substrate fluorescein derivative monophosphate ester, thereby producing a fluorescein derivative monophosphate ester hydrolysate. The fluorescein derivative monophosphate ester hydrolysate is a fluorescent substance that emits fluorescence when irradiated with excitation light. Therefore, the specimen can be detected by detecting the fluorescence emitted from the hydrolysate upon excitation.

Since the fluorescence from a fluorescent substance is strong, a very small amount of substance can be detected. Therefore, the method according to the present invention can detect a very small amount of an enzyme-specimen complex, thereby improving detection sensitivity.

The method of the invention is able to detect nucleic acids including DNA and RNA, proteins, or protein nucleic acid complexes.

The method of the invention is suitable for detection of a specimen that is present in liquid phase, fixed to a solid-phase support, present in a cell, or present in a chromosome, or the like.

The above-described method of detecting nucleic acids or the like can be applied to, for example, gene location determination, gene structural analysis, and detection of a viral gene, using a probe of a known base sequence. Regarding protein detection, the method of the invention can be applied to study virus infections or allergies, clinical laboratory tests, and the like.

The preferred fluorescein derivative monophosphate ester hydrolysate used by the method of the invention may have a structure represented by one of Formulas V to VIII below to further improve detection sensitivity.

(V)

(VI)

(VII)

(VIII)

The excitation light for irradiation of the fluorescein derivative monophosphate ester hydrolysate is electromagnetic radiation that excites the fluorescent substance produced by the hydrolysis and causes emission of fluorescence.

The fluorescence can be detected by visual observation, a fluorescence spectrophotometer, a camera (such as a CCD (charge-coupled device) camera or an instant camera), or the like.

According to another aspect of the invention, there is provided a method of detecting nucleic acids, proteins, protein nucleic acid complexes or the like. The method comprises the steps of: binding an enzyme to a specimen of nucleic acid, protein, protein nucleic acid complex or the like; reacting a fluorescein derivative diphosphate ester with the enzyme bound to the specimen to form a hydrolysate of the fluorescein derivative diphosphate ester; and irradiating the hydrolysate with excitation light to detect fluorescence emitted from the hydrolysate.

Any fluorescein derivative diphosphate ester known in the art may be used in the method of the present invention. Preferably, the fluorescein derivative diphosphate ester has a structure represented by one of Formulas IX to XII below:

(IX)

(X)

In this method, the enzyme bound to the specimen is reacted with a fluorescein derivative diphosphate ester, preferably one represented by one of Formulas IX to XII. This enzyme-substrate reaction breaks the ester linkage of the substrate fluorescein derivative diphosphate ester, thereby producing a fluorescein derivative diphosphate ester hydrolysate. The fluorescein derivative diphosphate ester hydrolysate is a fluorescent substance that emits fluorescence when irradiated with excitation light. Therefore, the specimen can be detected by detecting the fluorescence emitted from the hydrolysate upon excitation.

Since the fluorescence from a fluorescent substance is strong, a very small amount of substance can be detected. Therefore, the method of the present invention can detect a very small amount of an enzyme-specimen complex, thereby improving detection sensitivity.

The method of the invention is able to detect nucleic acids, proteins, or protein nucleic acid complexes.

The method of the invention is suitable for detection of a specimen that is present in liquid phase, fixed to a solid-phase support, present in a cell, or present in a chromosome, or the like.

The above-described method of detecting nucleic acids or the like can be applied to, for example, gene location determination, gene structural analysis, and detection of a viral gene, using a probe of a known base sequence. Regarding protein detection, the method can be applied to study virus infections or allergies, clinical laboratory tests, and the like.

Examples of the enzyme to be reacted with the fluorescein derivative include alkaline phosphatase, acid phosphatase, β-galactosidase, esterase, peroxidase, and sugar chain nicking enzymes. Examples of the sugar chain nicking enzymes include α-glucosidase, β-glucosidase, α-glucuronidase, and β-glucuronidase. These enzymes break the ester linkage of the fluorescein derivative phosphate ester.

The enzyme is bound to the specimen by, for example, a method in which a hapten bound to a specimen and the enzyme bound to an anti-hapten antibody are bound by an antigen-antibody reaction.

Examples of the hapten suitable for the method of the invention include biotin, digoxigenin, dinitrophenol, trinitrophenol, fluorescein, tetramethyl rhodamine, isothiocyanate, rhodamine, coumarin, DNA, RNA and virus.

DETAILED DESCRIPTION OF PREFERRED EMBODIMENTS

Preferred embodiments of the present invention will be described in detail hereinafter with reference to the accompanying drawing.

First Preferred Exemplary Embodiment

A first preferred embodiment of the method of detecting nucleic acids or the like according to the present invention, binds an alkaline phosphatase to a λDNA specimen, then reacts a fluorescein derivative monophosphate ester with the alkaline phosphatase, and then irradiates the reaction product with excitation light to detect the emitted fluorescence.

The fluorescein derivative monophosphate ester according to this embodiment is phosphorylated 5-(4-biphenylcarboxamido)-3'-O-(1-naphthyl)methylfluorescein represented by Formula I below:

An example of the DNA detection method according to the first preferred embodiment will be described below.

1) First described will be the synthesis of phosphorylated 5-(4-biphenylcarboxamido)-3'-O-(1-naphthyl)methylfluorescein represented by Formula I.

First, 202 mg (1.019 mmol) of 4-phenylbenzoic acid was placed in a 30 ml-Kjeldahl flask, which was then sealed by a serum cap (Ceptor Rubber, made by Aldrich). After the air inside the flask was replaced with argon gas, 2 ml of dehydrated and distilled dichloroethane was added and the mixture was vigorously stirred under the atmosphere of argon.

Then, a catalytic amount of benzyltriethylammonium chloride was added as a phase transfer catalyst. After 81.4 μl (1.121 mmol) of thionyl chloride was added, the mixture was heated and refluxed for 3 hours.

After the reaction, an excess of thionyl chloride was removed by vacuum distillation. The remaining mixture was vacuum-dried, thus obtaining 4-biphenylcarbonyl chloride as a first intermediate product at a yield of 80%.

Next, 176.7 mg (0.815 mmol) of the first intermediate product is placed in a 10 ml-Kjeldahl flask, which was then sealed with a serum cap. After the air inside the flask was replaced with argon gas, 1 ml of dehydrated and distilled acetone was added and the mixture was vigorously stirred under the atmosphere of argon.

After 283 mg (0.815 mmol) of 5-aminofluorescein was added, the mixture was stirred at room temperature for 12 hours, thereby producing 5-(4-biphenylcarboxamido) fluorescein as a second intermediate product.

The second intermediate product was separated by silica gel column chromatography. The yield of the second intermediate product was 97.2%. The structure of the second intermediate product was confirmed by $^1$H-NMR, IR and MS spectra.

Then, 57.9 mg (0.11 mmol) of 5-(4-biphenyl carboxamido)fluorescein was placed in a 10 ml-Kjeldahl flask, which was then sealed with a serum cap. The air inside the flask was then replaced with argon. Under the argon atmosphere, 400 µl of dehydrated and distilled DMF was added and the mixture was stirred until it dissolved.

Then, 29.5 mg (0.167 mmol) of 1-(chloromethyl) naphthalene was added, and the solution was stirred at room temperature for 10 hours, thus producing 5-(4-biphenylcarboxamido)-3'-O-(1-naphthyl)methylfluorescein as a third intermediate product.

The third intermediate product was separated by reversed-phase silica gel column chromatography. The yield of the third intermediate product was 41%. The structure of the third intermediate product was confirmed by $^1$H-NMR, IR and MS spectra.

After that, 23.1 mg (0.0346 mmol) of the third intermediate product was placed in a 10 ml-Kjeldahl flask, which was then sealed with a serum cap. The air inside the flask was replaced with argon gas. The flask was cooled to 0° C. and 300 µl of dehydrated and distilled pyridine was added under the argon atmosphere. Subsequently, 6.6 µl (0.0708 mmol) of phosphorus oxychloride was added at 0° C., and the mixture was stirred at 0° C. for an hour. The reaction solution was then put into cooled distilled water to stop the reaction. Thereby, phosphorylated 5-(4-biphenylcarboxamido)-3'-O-(1-naphthyl)methylfluorescein was obtained as a final product. The final product was separated by reversed-phase silica gel column chromatography (solvent: water/methanol).

The yield of the final product was 67%. The structure of the final product was confirmed by $^1$H-NMR, IR and MS spectra.

2) Detection of λDNA was performed using phosphorylated 5-(4-biphenylcarboxamido)-3'-O-(1-naphthyl) methylfluorescein synthesized as described above. The detection limit amount was determined by spot tests described below.

First, the λDNA was labeled with digoxigenin (hereinafter referred to as "DIG"), using DNA Labeling & Detection Kit (Berlinger-Mannheim). The labeled λDNA was diluted with tris buffer (10 mM tris (pH 8) 1 mM EDTA) to prepare DNA solutions having a concentration of 0 fg(femtogram)/µl, 5 fg/µl, 10 fg/µl, 20 fg/µl, 40 fg,µl, 80 fg/µl, and 400 fg/µl.

For uniform dilution of the labeled λDNA, the tris buffer contained herring sperm DNA as a non-specific DNA. The quantity of herring sperm DNA was adjusted such that 50 ng of herring sperm DNA would be present in each spot on the nylon membrane (described below).

Figure 1:
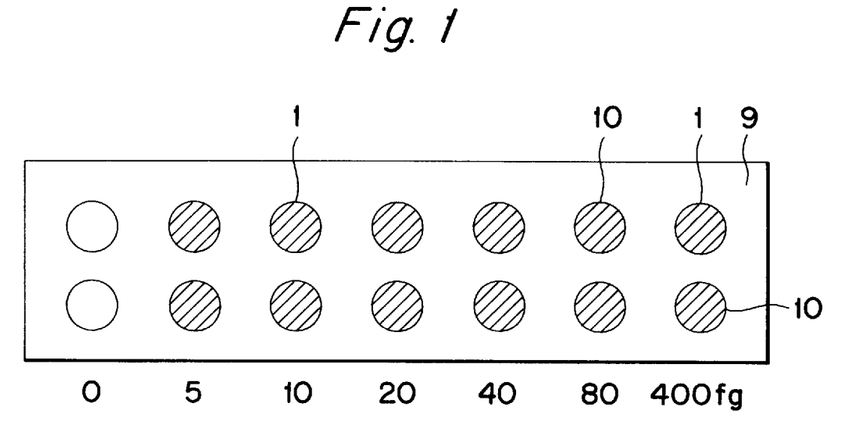
FIG. 1 illustrates a spotted nylon membrane indicating the result of an example of the first preferred DNA detection method according to the present invention.

A nylon membrane 9 (3 cm×7 cm, Biodyne A, 0.45 µM, Pall) was spotted with 1 µl of the individual DNA solutions, as shown in FIG. 1, so that the individual spots were provided with 0 fg, 5 fg, 10 fg, 20 fg, 40 fg, 80 fg or 400 fg of the specimen λDNA. The spots of 0 fg were provided for blank tests. In FIG. 1, the spots of the DNA solutions were denoted by reference numeral 1.

The nylon membrane was heated and kept at 80° C. for 30 minutes under vacuum. After being dipped in a 0.1% skim milk powder solution for 30 minutes, the nylon membrane was treated with alkaline phosphatase-labeled anti-DIG-Fab fragments for 30 minutes. The nylon membrane was then washed three times with a buffer (0.1M tris, pH 7.5, 0.15M NaCl) for 10 minutes each.

Then, 2 ml of a substrate solution (100 µg/ml, phosphorylated 5-(4-biphenylcarboxamido)-3'-O-(1-naphthyl) methylfluorescein (synthetic substrate) in 100 mM tris buffer, pH 8, 100 mM NaCl, 50 mM $MgCl_2$) was dipped on the nylon membrane so that the solution covered the entire surface of the membrane. The nylon membrane was covered with a parafilm, and left still in a dark room at 37° C. for an hour.

Thereby, the enzyme reaction between the synthetic substrate and the phosphatase was carried out. After the parafilm was removed, 0.5N NaOH was dipped on the nylon membrane to end the reaction. The enzyme reaction hydrolyzed the synthetic substrate represented by Formula I into a hydrolysate represented by Formula V, which was deposited on the nylon membrane.

The nylon membrane was irradiated with ultraviolet rays (302 nm, 2 mW/cm$^2$) to excite the reaction product. The fluorescence emitted was received by a CCD camera (VP-1500 by SONY) and recorded for printout.

If a spot became visible upon the UV irradiation, it was determined that fluorescence was detected in the spot. If a spot remained invisible, it was determined that fluorescence was not detected in the spot.

The result was that fluorescence 10 was detected in the spots having 5 fg or more of λDNA, as indicated in FIG. 1. Thus, the method of this example was able to detect 5 fg or more of λDNA.

Second Preferred Exemplary Embodiment

The DNA detection method according to a second preferred embodiment of the present invention differs from the method of the first embodiment in that the method of the second embodiment uses as a fluorescein derivative monophosphate ester, phosphorylated 5-(4-biphenylcarboxamido) -3'-O-(2-naphthyl)methylfluorescein represented by Formula II below:

(II)

An example of the DNA detection method according to the second embodiment will be described below.

1) First described will be the synthesis of phosphorylated 5-(4-biphenylcarboxamido)-3'-O-(2-naphthyl) methylfluorescein represented by Formula II.

The aforementioned second intermediate product, 5-(4-biphenylcarboxamido)fluorescein, was synthesized by the manner described in conjunction with the example of the first embodiment. Then, 57.9 mg (0.11 mmol) of 5-(4-biphenylcarboxamido)fluorescein was placed in a 10 ml-Kjeldahl flask, which was then sealed with a serum cap. The air inside the flask was than replaced with argon. Under the argon atmosphere, 400 µl of dehydrated and distilled DMF was added and the mixture was stirred until it dissolved.

Then, 29.5 mg (0.167 mmol) of 2-(chloromethyl) naphthalene was added, and the solution was stirred at room temperature for 10 hours, thus producing 5-(4-biphenylcarboxamido)-3'-O-(2-naphthyl)methylfluorescein as a third intermediate product.

The third intermediate product was separated by reversed-phase silica gel column chromatography. The yield of the third intermediate product was 41%. The structure of the third intermediate product was confirmed by $^1$H-NMR, IR and MS spectra.

After that, 23.1 mg (0.0346 mmol) of the third intermediate product was placed in a 10 ml-Kjeldahl flask, which was then sealed with a serum cap. The air inside the flask was then replaced with argon gas. The flask was cooled to 0° C. and 300 µl of dehydrated and distilled pyridine was added under the argon atmosphere. Subsequently, 6.6 µl (0.0708 mmol) of phosphorus oxychloride was added at 0° C., and the mixture was stirred at 0° C. for an hour. The reaction solution was then put into cooled distilled water to stop the reaction. Thereby, phosphorylated 5-(4-biphenylcarboxamido)-3'-O-(2-naphthyl)methylfluorescein was obtained as a final product. The final product was separated by reversed-phase silica gel column chromatography (solvent: water/methanol).

The yield of the final product was 67%. The structure of the final product was confirmed by $^1$H-NMR, IR and MS spectra.

2) Detection of λDNA was performed using phosphorylated 5-(4-biphenylcarboxamido)-3'-O-(2naphthyl) methylfluorescein represented by Formula II and following the procedure of the example in the first embodiment. By enzyme reaction, the synthetic substrate represented by Formula II was hydrolyzed into a hydrolysate represented by Formula VI, which was deposited on a nylon membrane.

(VI)

As in the example of the first embodiment, the nylon membrane was irradiated with ultraviolet rays, and the light emitted from the hydrolysate was detected. The result showed that the method of this example was able to detect 5 fg or more of λDNA.

According to the methods explained above, which use a fluorescein derivative monophosphate ester represented by Formula I (first embodiment) or Formula II (second embodiment), a resolving power is also improved. That is the reason that the hydrolysate represented by Formula V or Formula VI of the fluorescein derivative monophosphate ester represented by Formula I or Formula II is strongly deposited on the nylon membrane.

Third Preferred Exemplary Embodiment

The DNA detection method according to a third preferred embodiment of the present invention differs from the method of the first embodiment in that the method of the third embodiment uses as a fluorescein derivative monophosphate ester, 3'-(2,4-dimethylbenzyloxy)-6'-hydroxy-5-(4-biphenylcarboxamido)fluorescein phosphate, represented by Formula III below:

(III)

An example of the DNA detection method according to the third embodiment will be described below.

1) First described will be the synthesis of 3'-(2,4-dimethylbenzyloxy)-6'-hydroxy-5-(4-biphenylcarboxamido)fluorescein phosphate mentioned above.

The aforementioned second intermediate product, 5-(4-biphenylcarboxamido)fluorescein, was synthesized by the manner described in conjunction with the example of the first embodiment. Then, 59.0 mg (0.112 mmol) of the second intermediate product was placed in a 10 ml-Kjeldahl flask, which was then sealed with a serum cap. The air inside the flask was replaced with argon. Under the argon atmosphere, 400 µl of dehydrated and distilled DMF was added and the mixture was stirred until it dissolved. After 21.0 µl (0.144 mmol) of 2,4-dimethylbenzyl chloride was added, the solution was stirred at room temperature for 10 hours, thus producing 3'-(2,4-dimethylbenzyloxy)-6'-hydroxy-5-(4-biphenylcarboxamido)fluorescein as a third intermediate product. The third intermediate product was separated by reversed-phase silica gel column chromatography. The yield was 54%. The structure of the third intermediate product was confirmed by $^1$H-NMR, IR and MS spectra.

After that, 31.9 mg (0.0494 mmol) of the third intermediate product was placed in a 10 ml-Kjeldahl flask, which was then sealed with a serum cap. The air inside the flask was replaced with argon gas. The flask was cooled to 0° C. and 300 μl of dehydrated and distilled pyridine was added under the argon atmosphere.

Subsequently, 7.0 μl (0.0751 mmol) of phosphorus oxychloride was added at 0° C., and the mixture was stirred at 0° C. for an hour. The reaction solution was then put into cooled distilled water to stop the reaction. Thereby, 3'-(2,4-dimethylbenzyloxy)-6'-hydroxy-5-(4-biphenylcarboxamido)fluorescein phosphate was obtained as a final product. The final product was separated by reversed-phase silica gel column chromatography (solvent: water/methanol).

The yield of the final product was 53%. The structure of the final product was confirmed by ¹H-NMR, IR and MS spectra.

2) Detection of λDNA was performed using 3'-(2,4-dimethylbenzyloxy)-6'-hydroxy-5-(4-biphenylcarboxamido) fluorescein phosphate and following the procedure of the example in the first embodiment. By enzyme reaction, the synthetic substrate represented by Formula III was hydrolyzed into a hydrolysate represented by Formula VII, which was deposited on a nylon membrane.

(VII)

As in the example of the first embodiment, the nylon membrane was irradiated with ultraviolet rays, and the light emitted from the hydrolysate was detected. The result showed that the method of this example was able to detect 5 fg or more of λDNA.

Fourth Preferred Exemplary Embodiment

The DNA detection method according to a fourth preferred embodiment of the present invention differs from the method of the first embodiment in that the method of the fourth embodiment uses as a fluorescein derivative monophosphate ester, 3'-(3,4-dimethyl benzyloxy)-6'-hydroxy-5-(4-biphenylcarboxamido) fluorescein phosphate represented by Formula IV below:

(IV)

An example of the DNA detection method according to the fourth embodiment will be described below.

1) First described will be the synthesis of 3'-(3,4-dimethylbenzyloxy)-6'-hydroxy-5-(4-biphenyl carboxamido)fluorescein phosphate mentioned above.

The aforementioned second intermediate product, 5-(4-biphenylcarboxamido)fluorescein, was synthesized by the manner described in conjunction with the example of the first embodiment. Then, 41.0 mg (0.0777 mmol) of 5-(4-biphenylcarboxamido)fluorescein was placed in a 10 ml-Kjeldahl flask, which was then sealed with a serum cap. The air inside the flask was replaced with argon. Under the argon atmosphere, 400 μl of dehydrated and distilled DMF was added and the mixture was stirred until it dissolved.

Then, 20.0 μl (0.137 mmol) of 2,4-dimethylbenzyl chloride was added, and the solution was stirred at room temperature for 10 hours, thus producing 3'-(3,4-dimethylbenzyloxy)-6'-hydroxy-5-(4-biphenylcarboxamido) fluorescein as a third intermediate product. The third intermediate product was separated by reversed-phase silica gel column chromatography. The yield of the third intermediate product was 64%. The structure of the third intermediate product was confirmed by ¹H-NMR, IR and MS spectra.

After that, 17.3 mg (0.0268 mmol) of the third intermediate product was placed in a 10 ml-Kjeldahl flask, which was then sealed with a serum cap. The air inside the flask was then replaced with argon gas. The flask was cooled to 0° C. and 300 μl of dehydrated and distilled pyridine was added under the argon atmosphere. Subsequently, 5.0 μl (0.0536 mmol) of phosphorus oxychloride was added at 0° C., and the mixture was stirred at 0° C. for an hour. The reaction solution was then put into cooled distilled water to stop the reaction. Thereby, 3'-(3,4-dimethylbenzyloxy)-6'-hydroxy-5-(4-biphenylcarboxamido)fluorescein phosphate was obtained as a final product. The final product was separated by reversed-phase silica gel column chromatography (solvent: water/methanol).

The yield of the final product was 76%. The structure of the final product was confirmed by ¹H-NMR, IR and MS spectra.

2) Detection of λDNA was performed using 3'-(3,4-dimethylbenzyloxy)-6'-hydroxy-5-(4-biphenylcarboxamido) fluorescein phosphate and following the procedure of the example in the first embodiment. By enzyme reaction, the synthetic substrate represented by Formula IV was hydrolyzed into a hydrolysate represented by Formula VIII, which was deposited on a nylon membrane.

(VIII)

As in the example of the first embodiment, the nylon membrane was irradiated with ultraviolet rays, and the light emitted from the hydrolysate was detected. The result showed that the method of this embodiment was able to detect 5 fg or more of λDNA.

Fifth Preferred Exemplary Embodiment

The DNA detection method according to a fifth preferred embodiment of the present invention will be described. This embodiment differs from the first to fourth embodiments in that the fifth embodiment uses a fluorescein derivative diphosphate ester as the fluorescein derivative phosphate ester to be reacted with the enzyme. The fluorescein derivative diphosphate ester according to the fifth embodiment is 3',6'-dihydroxy-5-(2-methylphenyl)thioureidofluorescein diphosphate represented by Formula IX below:

An example of the DNA detection method according to the fifth embodiment will be described below.

1) First described will be the synthesis of 3',6'-dihydroxy-5-(2-methylphenyl)thioureidofluorescein diphosphate.

First, 55 mg (0.14 mmol) of fluorescein isocyanate was placed in a 10 ml-Kjeldahl flask, which was then sealed by a serum cap. After the air inside the flask was replaced with argon gas, 300 µl of dehydrated and distilled ethanol was added and the mixture was vigorously stirred under the atmosphere of argon, thus obtaining a fluorescein isocyanate solution.

Next, 15.7 µl (0.15 mmol) of 2-methylaniline was dissolved in 100 µl of dehydrated and distilled ethanol to obtain a 2-methylaniline solution. The 2-methylaniline solution was added to the fluorescein isocyanate solution in the Kjeldahl flask.

The solution in the Kjeldahl flask was stirred at room temperature for 12 hours, thus producing 3',6'-dihydroxy-5-(2-methylphenyl)thioureidofluorescein as a first intermediate product. The first intermediate product was separated by silica gel column chromatography. The yield of the first intermediate product was 90%. The structure of the first intermediate product was confirmed by $^1$H-NMR, IR and MS spectra.

Then, 55.6 mg (0.11 mmol) of the first intermediate product was placed in a 10 ml-Kjeldahl flask, which was then sealed with a serum cap. The air inside the flask was replaced with argon. The flask was cooled to 0° C. and 250 µl of dehydrated and distilled pyridine was added under the argon atmosphere. Subsequently, 31.3 µl (0.34 mmol) of phosphorus oxychloride was added, and the mixture was stirred at 0° C. for an hour. The reaction solution was then put into cooled distilled water to stop the reaction. Thereby, 3',6'-dihydroxy-5-(2-methylphenyl)thioureidofluorescein diphosphate was obtained as a final product. The final product was separated by reversed-phase silica gel column chromatography (solvent: water/methanol).

The yield of the final product was 89%. The structure of the final product was confirmed by $^1$H-NMR, IR and MS spectra.

2) Detection of λDNA was performed using 3',6'-dihydroxy-5-(2-methylphenyl)thioureidofluorescein diphosphate and following the procedure of the example in the first embodiment. By enzyme reaction, the synthetic substrate represented by Formula IX was hydrolyzed into a hydrolysate, which was deposited on a nylon membrane.

As in the example of the first embodiment, the nylon membrane was irradiated with ultraviolet rays, and the light emitted from the hydrolysate was detected. The result showed that the method of this example was able to detect 80 fg or more of λDNA.

Sixth Preferred Exemplary Embodiment

The DNA detection method according to a sixth preferred embodiment of the present invention differs from the method of the fifth embodiment in that the method of the sixth embodiment uses as a fluorescein derivative diphosphate ester, 3',6'-dihydroxy-5-( 3,5-dimethylphenyl)thioureido fluorescein diphosphate represented by Formula X below:

An example of the DNA detection method according to the sixth embodiment will be described below.

1) First described will be the synthesis of 3',6'-dihydroxy-5-(3,5-dimethylphenyl)thioureido fluorescein diphosphate.

First, 100 mg (0.26 mmol) of fluorescein isocyanate was placed in a 10 ml-Kjeldahl flask, which was then sealed by a serum cap. After the air inside the flask was replaced with argon gas, 300 µl of dehydrated and distilled ethanol was added and the mixture was vigorously stirred under the atmosphere of argon, thus obtaining a fluorescein isocyanate solution.

Next, 32.3 µl (0.26 mmol) of 3,5-dimethylaniline was dissolved in 100 µl of dehydrated and distilled ethanol to obtain a 3,5-dimethylaniline solution. The 3,5-dimethylaniline solution was added to the fluorescein isocyanate solution in the Kjeldahl flask.

The solution in the Kjeldahl flask was stirred at room temperature for 12 hours, thus producing 3',6'-dihydroxy-5-(3,5-dimethylphenyl)thioureidofluorescein as a first intermediate product. The first intermediate product was separated by silica gel column chromatography. The yield of the first intermediate product was 91%. The structure of the first intermediate product was confirmed by $^1$H-NMR, IR and MS spectra.

Then, 50 mg (0.1 mmol) of the first intermediate product was placed in a 10 ml-Kjeldahl flask, which was then sealed with a serum cap. The air inside the flask was replaced with argon. The flask was cooled to 0° C. and 250 µl of dehydrated and distilled pyridine was added under the argon atmosphere. Subsequently, 18.6 µl (0.2 mmol) of phosphorus oxychloride was added, and the mixture was stirred at 0° C. for an hour. The reaction solution was then put into cooled distilled water to stop the reaction. Thereby, 3',6'-dihydroxy-5-(3,5-dimethylphenyl)thioureidofluorescein diphosphate was obtained as a final product. The final product was separated by reversed-phase silica gel column chromatography (solvent: water/methanol).

The yield of the final product was 90%. The structure of the final product was confirmed by $^1$H-NMR, IR and MS spectra.

2) Detection of λDNA was performed using 3',6'-dihydroxy-5-(3,5-dimethylphenyl)thioureidofluorescein diphosphate and following the procedure of the example in the first embodiment. By enzyme reaction, the synthetic substrate represented by Formula X was hydrolyzed into a hydrolysate, which was deposited on a nylon membrane.

As in the example of the first embodiment, the nylon membrane was irradiated with ultraviolet rays, and the light emitted from the hydrolysate was detected. The result showed that the method of this example was able to detect 20 fg or more of λDNA.

Seventh Preferred Exemplary Embodiment

The DNA detection method according to a seventh preferred embodiment of the present invention differs from the method of the fifth embodiment in that the method of the seventh embodiment uses as a fluorescein derivative diphosphate ester, 3',6'-dihydroxy-5-(2-biphenylcarboxamido) fluorescein diphosphate represented by Formula XI below:

(XI)

An example of the DNA detection method according to the seventh embodiment will be described below.

1) First described will be the synthesis of 3',6'-dihydroxy-N-(2-biphenylcarbonyl)-5-amino fluorescein diphosphate.

First, 202 mg (1.019 mmol) of 2-phenylbenzoic acid was placed in a 30 ml-Kjeldahl flask, which was then sealed by a serum cap. After the air inside the flask was replaced with argon gas, 2 ml of dehydrated and distilled dichloroethane was added and the mixture was vigorously stirred at room temperature under the atmosphere of argon.

Then, a catalytic amount of benzyltriethylammonium chloride was added as a phase transfer catalyst. After 81.4 μl (1.121 mmol) of thionyl chloride was added, the mixture was heated and refluxed for 3 hours. After the reaction, an excess of thionyl chloride was removed by vacuum distillation. The remaining mixture was vacuum-dried, thus obtaining 2-biphenylcarbonyl chloride as a first intermediate product at a yield of 80%.

Next, 176.7 mg (0.815 mmol) of the first intermediate product was placed in a 10 ml-Kjeldahl flask, which was then sealed with a serum cap. After the air inside the flask was replaced with argon gas, 1 ml of dehydrated and distilled acetone was added and the mixture was vigorously stirred under the atmosphere of argon.

After 283 mg (0.815 mmol) of 5-aminofluorescein was added, the mixture was stirred at room temperature for 12 hours, thereby producing N-(2-biphenylcarbonyl)-5-aminofluorescein as a second intermediate product. The second intermediate product was separated by silica gel column chromatography. The yield of the second intermediate product was 95%. The structure of the second intermediate product was confirmed by $^1$H-NMR, IR and MS spectra.

Then, 13 mg (0.024 mmol) of the second intermediate product was placed in a 10 ml-Kjeldahl flask, which was then sealed with a serum cap. The air inside the flask was replaced with argon. The flask was cooled to 0° C. and 100 μl of dehydrated and distilled pyridine was added under the argon atmosphere. Subsequently, 6.6 μl (0.07 mmol) of phosphorus oxychloride was added, and the mixture was stirred at 0° C. for an hour. The reaction solution was then put into cooled distilled water to stop the reaction. Thereby, 3',6'-dihydroxy-N-(2-biphenylcarbonyl)-5-aminofluorescein diphosphate was obtained as a final product. The final product was separated by reversed-phase silica gel column chromatography (solvent: water/methanol).

The yield of the final product was 80%. The structure of the final product was confirmed by $^1$H-NMR, IR and MS spectra.

2) Detection of λDNA was performed using 3',6'-dihydroxy-N-(2-biphenylcarbonyl)-5-aminofluorescein diphosphate and following the procedure of the example in the first embodiment. By enzyme reaction, the synthetic substrate represented by Formula XI was hydrolyzed into a hydrolysate, which was deposited on a nylon membrane.

As in the first example, the nylon membrane was irradiated with ultraviolet rays, and the light emitted from the hydrolysate was detected. The result showed that the method of this example was able to detect 20 fg or more of λDNA.

Eighth Preferred Exemplary Embodiment

The DNA detection method according to an eighth preferred embodiment of the present invention differs from the method of the fifth embodiment in that the method of the eighth embodiment uses as a fluorescein derivative diphosphate ester, 3',6'-dihydroxy-N-(4-biphenylcarbonyl)-5-aminofluorescein diphosphate represented by Formula XII below:

(XII)

An example of the DNA detection method according to the eighth embodiment will be described below.

1) First described will be the synthesis of 3',6'-dihydroxy-5-(4-biphenylcarboxamido)fluorescein diphosphate.

First, 202 mg (1.019 mmol) of 4-phenylbenzoic acid was placed in a 30 ml-Kjeldahl flask, which was then sealed by a serum cap. After the air inside the flask was replaced with argon gas, 2 ml of dehydrated and distilled dichloroethane was added and the mixture was vigorously stirred at room temperature under the atmosphere of argon.

Then, a catalytic amount (300 μg) of benzyltriethylammonium chloride was added as a phase transfer catalyst. After 81.4 μl (1.121 mmol) of thionyl chloride was added, the mixture was heated and refluxed for 3 hours. After the reaction, an excess of thionyl chloride was removed by vacuum distillation. The remaining mixture was vacuum-dried, thus obtaining 4-biphenylcarbonyl chloride as a first intermediate product at a yield of 80%.

Next, 176.7 mg (0.815 mmol) of the first intermediate product is placed in a 10 ml-Kjeldahl flask, which was then sealed with a serum cap. After the air inside the flask was replaced with argon gas, 1 ml of dehydrated and distilled acetone was added and the mixture was vigorously stirred under the atmosphere of argon.

After 283 mg (0.815 mmol) of 5-aminofluorescein was added, the mixture was stirred at room temperature for 12 hours, thereby producing N-(4-biphenylcarbonyl)-5-aminofluorescein as a second intermediate product. The second intermediate product was separated by silica gel column chromatography. The yield of the second intermediate product was 98%. The structure of the second intermediate product was confirmed by $^1$H-NMR, IR and MS spectra.

Then, 50 mg (0.095 mmol) of the second intermediate product was placed in a 10 ml-Kjeldahl flask, which was then sealed with a serum cap. The air inside the flask was replaced with argon. The flask was cooled to 0° C. and 250 µl of dehydrated and distilled pyridine was added under the argon atmosphere. Subsequently, 26.6 µl (0.29 mmol) of phosphorus oxychloride was added, and the mixture was stirred at 0° C. for an hour. The reaction solution was then put into cooled distilled water to stop the reaction. Thereby, 3',6'-dihydroxy-N-(4-biphenylcarbonyl)-5-aminofluorescein diphosphate was obtained as a final product. The final product was separated by reversed-phase silica gel column chromatography (solvent: water/methanol).

The yield of the final product was 85%. The structure of the final product was confirmed by $^1$H-NMR, IR and MS spectra.

2) Detection of λDNA was performed using 3',6'-dihydroxy-N-(4-biphenylcarbonyl)-5-aminofluorescein diphosphate and following the procedure of the example in the first embodiment. By enzyme reaction, the synthetic substrate represented by Formula XII was hydrolyzed into a hydrolysate, which was deposited on a nylon membrane.

As in the example of the first embodiment, the nylon membrane was irradiated with ultraviolet rays, and the light emitted from the hydrolysate was detected. The result showed that the method of this example was able to detect 20 fg or more of λDNA.

The DNA detection results of the examples of the first to eighth embodiments are summarized in Table 1 below. In Table 1, "+" indicates that λDNA was detected, and "−" indicates that λDNA was not detected. In addition, "F1" to "F4" and "F9" to "F12" indicate the fluorescein derivative phosphate esters used in the examples represented by Formulas I to IV and XI to XII, respectively, and "F5" to "F8" indicate the fluorescein derivative phosphate ester hydrolysates represented by Formulas V to VIII, respectively.

Table 1 shows that the embodiments of the method of detecting nucleic acids or the like of the present invention are able to detect a small amount of λDNA such as 5 to 400 fg.

TABLE 1

| Example No. | Sub-strate | Hydro-lysate | Quantity of λDNA (fg) | | | | | | |
|---|---|---|---|---|---|---|---|---|---|
| | | | 0 | 5 | 10 | 20 | 40 | 80 | 400 |
| 1 | F1 | F5 | − | + | + | + | + | + | + |
| 2 | F2 | F6 | − | + | + | + | + | + | + |
| 3 | F3 | F7 | − | + | + | + | + | + | + |
| 4 | F4 | F8 | − | + | + | + | + | + | + |
| 5 | F9 | | − | − | − | − | − | + | + |
| 6 | F10 | | − | − | − | + | + | + | + |
| 7 | F11 | | − | − | − | + | + | + | + |
| 8 | F12 | | − | − | − | + | + | + | + |

As understood from the above description, each of the first to fourth embodiments reacts one of the fluorescein derivative monophosphate esters represented by Formulas I to IV with the enzyme bound to a specimen, and irradiates the fluorescein derivative monophosphate ester hydrolysate produced by the enzyme reaction with excitation light to detect fluorescence emitted from the hydrolysate. Thus, the embodiments are able to detect nucleic acids or the like with high detection sensitivities.

In addition, each of the fifth to eighth embodiments reacts one of the fluorescein derivative diphosphate esters represented by Formulas IX to XII with the enzyme bound to a specimen, and irradiates the fluorescein derivative diphosphate ester hydrolysate produced by the enzyme reaction with excitation light to detect fluorescence emitted from the hydrolysate. Thus, the embodiments are able to detect nucleic acids or the like with high detection sensitivities.

While the present invention has been described with reference to what are presently considered to be preferred embodiments thereof, it is to be understood that the invention is not limited to the disclosed embodiments or examples. To the contrary, the invention is intended to cover various modifications and equivalent arrangements included within the spirit and scope of the appended claims.

What is claimed is:

1. A method of detecting nucleic acids, proteins, or protein nucleic acid complexes, said method comprising the steps of:

binding an enzyme to a specimen of nucleic acid, protein, or protein nucleic acid complex;

reacting a substituted fluorescein monophosphate having a structure represented by one of Formulas I to IV below:

(I)

(II)

(III)

and

-continued (IV)

with the enzyme bound to the specimen of nucleic acid, protein, or protein nucleic acid complex on a nylon membrane so as to deposit a hydrolysate of the substituted fluorescein monophosphate on said nylon membrane; and irradiating the hydrolysate with excitation light to detect fluorescence emitted from the hydrolysate on said nylon membrane.

2. The method according to claim 1, wherein the hydrolysate of the substituted fluorescein monophosphate has a structure represented by one of Formulas V to VIII below:

3. A method of detecting nucleic acids, proteins, or protein nucleic acid complexes, said method comprising the steps of:

binding an enzyme to a specimen of nucleic acid, protein, or protein nucleic acid complex;

reacting a 5-substituted fluorescein diphosphate with the enzyme bound to the specimen to form a hydrolysate of the 5-substituted fluorescein diphosphate; and irradiating the hydrolysate with excitation light to detect fluorescence emitted from the hydrolysate.

4. The method according to claim 3, wherein the specimen of nucleic acid, protein, or protein nucleic acid complex is on a nylon membrane and the hydrolysate is deposited on said nylon membrane.

5. The method according to claim 3, wherein the substituted fluorescein diphosphate has a structure represented by one of Formulas IX to XII below:

* * * * *